United States Patent [19]

Eguchi et al.

[11] Patent Number: 5,138,103
[45] Date of Patent: Aug. 11, 1992

[54] PROCESS FOR PRODUCING TETRABROMOBISPHENOL A

[75] Inventors: Hisao Eguchi, Shinnanyo; Masashige Kubo, Tokyo; Noritaka Nagasaki, Shinnanyo; Koji Kunimoto, Tokuyama, all of Japan

[73] Assignee: Tosoh Corporation, Shinnanyo, Japan

[21] Appl. No.: 745,888

[22] Filed: Aug. 16, 1991

[30] Foreign Application Priority Data

Aug. 20, 1990 [JP] Japan .................................. 2-217027
May 9, 1991 [JP] Japan .................................. 3-132155

[51] Int. Cl.$^5$ ...................... C07C 39/16; C07C 39/367
[52] U.S. Cl. ..................................... 568/726; 568/722; 568/723; 568/729
[58] Field of Search ................. 568/722, 723, 726, 729

[56] References Cited

U.S. PATENT DOCUMENTS 4,701,568 10/1987 McKinnie et al. ................... 568/726
5,068,463 11/1991 Walter ................................. 568/726

FOREIGN PATENT DOCUMENTS 0380363 8/1990 European Pat. Off. ............ 568/726
0005745 1/1977 Japan ................................. 568/726
0042789 10/1977 Japan ................................. 568/726

Primary Examiner—Werren B. Lone
Attorney, Agent, or Firm—Oblon, Spivak, McClelland, Maier & Neustadt

[57] ABSTRACT

A process for producing tetrabromobisphenol A of high quality, which comprises brominating bisphenol A with bromine, wherein a solvent mixture comprising a hydrohalogenic acid and an alcohol, is used as the solvent for reaction. Also disclosed is a process for producing tetrabromobisphenol A of high quality, which comprises brominating bisphenol A with bromine in an alcohol, wherein the reaction temperature is set at a level of from −10° to +20° C., and water is added in an aging step.

7 Claims, No Drawings

PROCESS FOR PRODUCING TETRABROMOBISPHENOL A

The present invention related to a process for producing tetrabromobisphenol A (hereinafter referred to simply as TBA) of high quality having the hydrolyzable bromide content reduced and having the hue improved.

TBA is a compound useful as a flame retardant for e.g. epoxy resins and ABS resins. TBA is produced usually by the reaction of bisphenol A (hereinafter referred to simply as BPA) with bromine by means of an organic solvent such as a lower alkyl alcohol or a halogenated hydrocarbon. For the industrial purpose, methanol is used as the solvent for reaction in many cases, since formation of impurities is thereby relatively small. However, TBA crystals produced by such a conventional method usually contains a hydrolyzable bromide at a level of from about 100 to 2000 ppm.

TBA is used in a large amount as a reactive-type flame retardant for an epoxy resin composition. TBA is incorporated alone or in the form of an epoxy resin having TBA as the backbone. However, in such use for epoxy resins, there is a problem that the hydrolyzable bromide contained in TBA adversely affect the curing reaction of the resins or the resin properties after the curing.

Especially in the case of epoxy resins for electrical or electronic materials such as laminates or encapsulating agents, the presence of such hydrolyzable bromide creates a serious problem. Namely, when TBA having a large content of the hydrolyzable bromide is used for an epoxy resin for an electrical or electronic material, the bromine content tends to be liberated as bromine ions due to e.g. moisture, and the liberated bromine ions bring about corrosion of metal, thus impairing the reliability of the material. Further, the hydrolyzable bromide in TBA acts as a catalyst poison in the curing reaction of the epoxy resin and thus causes a decrease in the curing rate.

Accordingly, TBA to be used for such application, is required to be purified by e.g. recrystallization to reduce the hydrolyzable bromide content. Japanese Unexamined Patent Publication No. 3139/1989 proposes, as an especially effective purification method, a method for treating TBA by contacting TBA dissolved under heating in an aromatic hydrocarbon, with an aqueous alkali metal solution. However, even when this purification method is carried out, the resulting TBA still contains from 50 to 100 ppm of the hydrolyzable bromide, and as such, it is not necessarily satisfactory for application to electrical or electronic materials. Further, this method requires a special purification step, and it is cumbersome and not economical from the industrial point of view.

On the other hand, the present inventors have previously found that in the process for producing TBA, TBA having the hydrolyzable bromide content reduced, can be obtained by using methanol containing from 5 to 15% by weight of water, as the solvent for reaction, and have previously filed a patent application (Japanese Patent Application No. 328168/1989).

Such a process is industrially convenient and is effective as a method for reducing the hydrolyzable bromide content. However, the resulting TBA is slightly colored. Therefore, it is not fully satisfactory as a process for producing high quality TBA.

Namely, when water is contained in the solvent for reaction, hypobromous acid will form in the system by the reaction as identified by the following reaction formula 1, and in the reaction system, not only the bromination reaction but also an oxidation reaction will take place, whereby there has been a problem that the product tends to be colored to some extent.

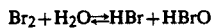
(Reaction formula 1)

It is an object of the present invention to provide a process for producing high quality TBA having the hydrolyzable bromide content reduced and having the improved, which has not been satisfied by any conventional process. Another object of the present invention is to provide an industrial process which is economically advantageous and which is a simplified form of the conventional process which required cumbersome process steps and was economically disadvantageous.

For the purpose of the present invention, the hydrolyzable bromide is represented by the amount of bromine ions dissociated when TBA is dissolved in a potassium hydroxide-methanol solution and refluxed for 15 minutes, as represented by the weight ratio of TBA.

The quantitative analysis of the amount of such bromine ions can be conducted by e.g. a potentiometric titration method by means of an aqueous silver nitrate solution, or by ion liquid chromatography.

Under these circumstances, the present inventors have conducted extensive studies to produce high quality TBA having the hydrolyzable bromide content reduced and having the hue improved on an industrial scale. As a result, it has been found possible to obtain high quality TBA in good yield by either (1) a process for producing tetrabromobisphenol A of high quality, which comprises brominating bisphenol A with bromine, wherein a solvent mixture comprising a hydrohalogenic acid and an alcohol, is used as the solvent for reaction, or (2) a process for producing tetrabromobisphenol A of high quality, which comprises brominating bisphenol A with bromine in an alcohol, wherein the reaction temperature is set at a level of from $-10$ to $+20°$ C., and water is added in an aging step.

Further, it has been found that according to the process of the present invention, the aging time can substantially be shortened as compared with the conventional process wherein an alcohol is used alone as the solvent for reaction, and the reaction of hydrogen bromide formed by the bromination reaction, with the alcohol as the solvent, can be suppressed. The present invention has been accomplished on the basis of these discoveries.

By applying the process of the present invention to the production of TBA, it is possible to reduce the hydrolyzable bromide content and to produce high quality TBA having the hue improved. Further, according to the process of the present invention, the aging time can substantially be shortened as compared with the conventional process wherein an alcohol is used alone as the solvent for reaction, and in addition, it is possible to suppress the reaction of hydrogen bromide formed by the bromination reaction, with the alcohol as the solvent.

The hydrolyzable bromide is believed to be derived from an alkyl bromide having a relatively weak carbon-bromine bond formed by the bromination of impurities in BPA and/or by bromination of side chain alkyl groups of TBA. Further this alkyl bromide is believed to be formed primarily by the reaction with bromine radicals.

The reason for the reduction of the hydrolyzable bromide content in the process of the present invention is not necessarily clear. However, it is considered that the addition of water to the reaction system suppresses the formation of bromine radicals, and consequently, formation of alkyl bromides causing the hydrolyzable bromide will also be suppressed.

On the other hand, the reason why TBA having the hue improved can be obtained by the process of the present invention, is believed to be such that the oxidation reaction in the reaction system is suppressed, and consequently, the coloring of the product will likewise be suppressed. Namely, it is believed that according to the process of the present invention, the equilibrium of the above mentioned reaction formula 1 tends to shift towards the original system, and the oxidation reaction in the reaction system is thereby suppressed.

Further, the reason why the aging time can substantially be shortened by the process of the present invention, is believed to be attributable to the effects of water added to the reaction system. Namely, the addition of water accelerates dissociation of hydroxyl groups of the substrate, whereby the reactivity with bromine cations is increased.

In addition, according to the process of the present invention, the equilibrium represented by the following reaction formula 2 tends to be shifted to the original system, and it is thereby possible to suppress the reaction of hydrogen bromide formed by the bromination reaction, with an alcohol as the solvent. For example, in the case of methanol frequently used as the solvent for reaction, the substance formed as a byproduct by the reaction formula 2 is methyl bromide. Methyl bromide is a substance having an extremely strong toxicity, and it is extremely important from the viewpoint of the operational environment and safety to reduce the amount of its formation.

  (Reaction formula 2)

Now, the present invention will be described in detail with reference to the preferred embodiments.

The solvent for reaction used in the first process of the present invention is a solvent mixture comprising a hydrohalogenic acid and an alcohol. The hydrohalogenic acid in the first process is hydrofluoric acid, hydrochloric acid, hydrobromic acid, hydroiodic acid or a mixture thereof, having a concentration of at least 5% by weight. Preferably, it is hydrochloric acid or hydrobromic acid. If the hydrohalogenic acid has a concentration of less than 5% by weight, the resulting TBA tends to be colored, such being undesirable. The alcohol used in this first process is a $C_{1-4}$ alcohol, preferably methanol.

Further, the mixing ratio of the hydrohalogenic acid and the alcohol varies depending upon the concentration of the hydrohalogenic acid. However, it is preferred to mix them so that the concentration of water in the solvent mixture will be from 3 to 20% by weight. If the concentration of water is less than 3% by weight, no adequate effect for reducing the hydrolyzable bromide will be obtained. On the other hand, if it exceeds 20% by weight, the purity of the resulting TBA tends to be low, such being undesirable. There is no particular restriction as to the substrate concentration of BPA in the solvent for reaction. However, it is usual that the substrate concentration is at a level of from 5 to 30% by weight.

The amount of bromine used in the first process is from 4.0 to 5.0 (mol ratio), preferably from 4.1 to 4.5, to BPA. If the amount is less than 4.0, the yield of TBA will be low. If it exceeds 5.0, a side reaction tends to take place due to the excess bromine, such being undesirable.

Bromine is added gradually usually over a period of from 0.5 to 10 hours. The reaction temperature at the time of the addition of bromine is from about $-10$ to $+50°$ C., particularly preferably from about $0°$ to $30°$ C. If the temperature is lower than $-10°$ C., the reaction tends to be very slow, and if it exceeds $50°$ C., side reactions such as decomposition of TBA tend to take place, such being undesirable.

After completion of the addition of bromine, aging is conducted usually for about 0.5 to 5 hours to complete the reaction. There is no particular restriction as to the reaction temperature during the aging. However, in order to suppress the reaction of hydrogen bromide with the alcohol, the temperature is selected usually within a range of from about $0°$ to $30°$ C.

On the other hand, the solvent for reaction to be used in the second process is a $C_{1-4}$ alcohol, preferably methanol. There is no particular restriction as to the substrate concentration of BPA in the alcohol, but the substrate concentration is usually from 5 to 30% by weight.

The reaction temperature in the second process is usually from $-10°$ to $+20°$ C., preferably from $0°$ to $15°$ C. If the temperature is lower than $-10°$ C., the reaction tends to be very slow, and if it exceeds $20°$ C., no adequate effect for reducing the hydrolyzable bromide will be obtained.

The amount of bromine and the method for its addition in the second process may be the same as in the first process. However, in the second process, after completion of the addition of bromine, aging is conducted usually for 0.5 to 5 hours while adding water, to complete the reaction. The amount of water to be added is usually from 2 to 15% by weight, preferably from 3 to 10% by weight, relative to the solvent for reaction. If the amount is less than 2% by weight, no adequate effect for reducing the hydrolyzable bromide will be obtained, and if it exceeds 15% by weight, the resulting TBA tends to be colored, such being undesirable. There is no particular restriction as to the manner of addition of water. Namely, it may be added all at once or may be added continuously.

In the process of the present invention, after completion of the reaction, water is added to the reaction solution to precipitate TBA dissolved in the reaction solution. The amount of water to be added is usually from about 30 to 100% by weight relative to the solvent for reaction. If the amount is less than 30% by weight, the amount of precipitation of TBA tends to be small, and if it exceeds 100% by weight, the purity of TBA tends to be low, such being undesirable.

In the process of the present invention, TBA crystals are separated by filtration from the reaction solution, then washed with water and dried to obtain a product.

TBA obtained by the process of the present invention, is high quality TBA containing only from 2 to 50 ppm of the hydrolyzable bromide and having the hue improved.

As is apparent from the forgoing description, according to the present invention, it is possible to produce in good yield high quality TBA having the hydrolyzable bromide content reduced and having the hue improved, which could not be obtained by conventional processes.

Accordingly, TBA obtained by the process of the present invention does not require a separate purification step and can be used directly as a flame retardant for resins for the application to electrical and electronical materials, such as laminates and encapsulating agents.

Further, as compared with a conventional method wherein an alcohol is used alone as the solvent for reaction, according to the process of the present invention, the reaction of hydrogen bromide formed by the bromination reaction, with the alcohol as the solvent, is substantially suppressed, whereby the recovery rates of the alcohol and hydrogen bromide after the reaction are substantially improved.

Accordingly, by the process of the present invention, high quality TBA can be produced industrially advantageously by simplifying the conventional process.

Now, the processes of the present invention will be described in detail with reference to Examples. However, it should be understood that the present invention is by no means restricted to such specific examples.

EXAMPLE 1

Into a four necked flask having a capacity of 1000 ml and equipped with a thermometer, a stirrer and a condenser, 54.8 g (0.24 mol) of BPA was charged, and 300 g of methanol and 40.6 g of 36 wt % hydrochloric acid were added thereto to dissolve BPA.

Then, while maintaining the reaction solution at 25° C., 163.0 g (1.02 mol) of bromine was dropwise added over a period of 4 hours, and aging was conducted at the same temperature for further 1 hour.

After the aging, remaining excess bromine was reduced by an addition of an aqueous hydrazine solution. Then, 250 g of water was added thereto over a period of 1 hour to precipitate TBA dissolved in the solution.

Then, precipitated crystals were collected by filtration, washed with water and dried to obtain 127.1 g of TBA as white crystals.

The isolated TBA crystals were analyzed by high performance liquid chromatography, whereby the purity of crystals was found to be 98.7%. Further, the crystals were subjected to potentiometric titration by means of an aqueous silver nitrate solution, whereby they were found to contain 21 ppm of a hydrolyzable bromide. Further, the analysis by means of a color difference meter was conducted, whereby the hue of the isolated crystals was found to have a Hunter whiteness of 95.9.

The reaction conditions are shown in Table 1, and the results obtained are shown in Table 2.

EXAMPLES 2 to 7

In the same manner as in Example 1, the reactions were conducted under the conditions as identified in Table 1. The results are shown in Table 2.

COMPARATIVE EXAMPLES 1 to 4

In the same manner as in Example 1, the reactions were conducted under the conditions as shown in Table 1. The results are shown in Table 2.

TABLE 1

| | Solvents for reaction | | | | Water/ water + methanol [1] (wt. %) | Reaction Temperature for dropwise addition of bromine (°C.) | Temperature for aging (°C.) |
| --- | --- | --- | --- | --- | --- | --- | --- |
| | Methanol (g) | Water (g) | Hydrohalogenic acid Type | (g) | | | |
| Example 1 | 300 | 0 | 36 wt % hydrochloric acid | 40.6 | 8.0 | 25 | 25 |
| Example 2 | 300 | 0 | 15 wt % hydrochloric acid | 30.6 | 8.0 | 25 | 25 |
| Example 3 | 300 | 0 | 47 wt % hydrobromic acid | 49.1 | 8.0 | 25 | 25 |
| Example 4 | 300 | 0 | 30 wt % hydrobromic acid | 37.1 | 8.0 | 10 | 10 |
| Example 5 | 300 | 0 | 30 wt % hydrobromic acid | 37.1 | 8.0 | 25 | 25 |
| Example 6 | 300 | 0 | 30 wt % hydrobromic acid | 37.1 | 8.0 | 25 | 40 |
| Example 7 | 280 | 0 | 30 wt % hydrobromic acid | 65.7 | 14.1 | 25 | 25 |
| Comparative Example 1 | 326 | 0 | — | 0 | 0 | 25 | 25 |
| Comparative Example 2 | 326 | 0 | — | 0 | 0 | 25 | 40 |
| Comparative Example 3 | 300 | 26 | — | 0 | 8.0 | 25 | 25 |
| Comparative Example 4 | 280 | 46 | — | 0 | 14.1 | 25 | 25 |

[1] Including water in the hydrohalogenic acid

TABLE 2

| | Results of reaction | | | | | | |
| --- | --- | --- | --- | --- | --- | --- | --- |
| | Isolated crystals of TBA | | | | | Methyl bromide | |
| | Yield (g) | Purity (wt. %) | Yield (mol %) | Hunter Whiteness | Hydrolyzable bromide (ppm) | Amount formed (g) | Yield [1] (mol %) |
| Example 1 | 127.1 | 98.7 | 96.1 | 95.9 | 21 | 0.3 | 0.3 |
| Example 2 | 126.7 | 99.1 | 96.2 | 95.7 | 28 | 0.2 | 0.2 |
| Example 3 | 127.9 | 99.8 | 97.8 | 96.2 | 12 | 0.2 | 0.2 |
| Example 4 | 127.8 | 99.5 | 97.4 | 96.3 | 3 | 0.1 | 0.1 |
| Example 5 | 128.1 | 99.6 | 97.7 | 96.2 | 15 | 0.2 | 0.2 |

TABLE 2-continued

| | Results of reaction | | | | | |
|---|---|---|---|---|---|---|
| | Isolated crystals of TBA | | | | Methyl bromide | |
| | Yield (g) | Purity (wt. %) | Yield (mol %) | Hunter Whiteness | Hydrolyzable bromide (ppm) | Amount formed (g) | Yield [1] (mol %) |
| Example 6 | 128.3 | 99.8 | 98.1 | 96.0 | 37 | 2.5 | 2.7 |
| Example 7 | 127.6 | 98.9 | 96.7 | 95.7 | 12 | 0.1 | 0.1 |
| Comparative Example 1 | 126.9 | 98.9 | 96.2 | 95.6 | 227 | 6.2 | 6.8 |
| Comparative Example 2 | 127.3 | 99.5 | 97.0 | 95.4 | 244 | 25.7 | 28.2 |
| Comparative Example 3 | 127.8 | 99.5 | 97.4 | 93.8 | 32 | 0.2 | 0.2 |
| Comparative Example 4 | 127.5 | 98.7 | 96.4 | 92.3 | 11 | 0.1 | 0.1 |

[1] Calculated from the resulting hydrogen bromide (theoretical value)

EXAMPLE 8

Into a four necked flask having a capacity of 1000 ml and equipped with a thermometer, a stirrer and a condenser, 54.8 g (0.24 mol) of BPA was charged and 320 g of methanol was added thereto to dissolve BPA.

Then, while maintaining the reaction solution at 10° C., 163.0 g (1.02 mol) of bromine was dropwise added over a period of 3 hours. After completion of the dropwise addition of bromine, aging was conducted at the same temperature for 15 minutes, and then 15 g of water was added thereto, and aging was conducted for further 2 hours.

After the aging, remaining excess bromine was reduced by an addition of an aqueous hydrazine solution. Then 250 g of water was added thereto over a period of 1 hour to precipitate TBA dissolved in the solution.

Then, precipitated crystals were collected by filtration, washed with water and dried to obtain 126.9 g of TBA as white crystals.

The isolated TBA crystals were analyzed by high performance liquid chromatography, whereby the purity of the crystals were found to be 99.3%. Further, the crystals were subjected to potentiometric titration by means of an aqueous silver nitrate solution, whereby they were found to contain 40 ppm of a hydrolyzable bromide. Further, the analysis was conducted by means of a color difference meter, whereby the hue of the isolated crystals was found to have a Hunter whiteness of 96.4.

The reaction conditions are shown in Table 3, and the results obtained are shown in Table 4.

EXAMPLES 9 to 14

In the same manner as in Example 8, the reactions were conducted under the conditions as shown in Table 3. The results are shown in Table 4.

COMPARATIVE EXAMPLES 5 to 10

In the same manner as in Example 8, the reactions were conducted under the conditions as shown in Table 3. The results are shown in Table 4.

TABLE 3

| | Solvent for reaction | | Reaction | | |
|---|---|---|---|---|---|
| | Methanol (g) | Water (g) | Temperature for dropwise addition of bromine (°C.) | Temperature for aging (°C.) | Amount of water added during the aging step (g) |
| Example 8 | 320 | 0 | 10 | 10 | 15 |
| Example 9 | 320 | 0 | 10 | 10 | 20 |
| Example 10 | 320 | 0 | 10 | 10 | 30 |
| Example 11 | 320 | 0 | 10 | 10 | 40 |
| Example 12 | 320 | 0 | 5 | 10 | 30 |
| Example 13 | 320 | 0 | 10 | 5 | 30 |
| Example 14 | 320 | 0 | 15 | 15 | 30 |
| Comparative Example 5 | 320 | 0 | 10 | 10 | 0 |
| Comparative Example 6 | 320 | 30 | 10 | 10 | 0 |
| Comparative Example 7 | 290 | 30 | 10 | 10 | 0 |
| Comparative Example 8 | 320 | 0 | 30 | 30 | 0 |
| Comparative Example 9 | 320 | 30 | 30 | 30 | 0 |
| Comparative Example 10 | 320 | 0 | 30 | 30 | 30 |

TABLE 4

| | Results of reaction | | | | |
| --- | --- | --- | --- | --- | --- |
| | Isolated crystals of TBA | | | | Methyl bromide Amount formed (g) |
| | Yield (g) | Purity (wt. %) | Yield (mol %) | Hunter Whiteness | Hydrolyzable bromide (ppm) | |
| Example 8 | 126.9 | 99.3 | 96.5 | 96.4 | 40 | 0.2 |
| Example 9 | 127.5 | 99.3 | 97.0 | 96.3 | 21 | 0.2 |
| Example 10 | 127.9 | 99.6 | 97.6 | 96.0 | 19 | 0.1 |
| Example 11 | 128.3 | 99.8 | 98.1 | 95.7 | 4 | 0.1 |
| Example 12 | 127.4 | 99.2 | 96.8 | 96.3 | 12 | 0.1 |
| Example 13 | 126.8 | 99.1 | 96.3 | 96.8 | 13 | 0.1 |
| Example 14 | 128.4 | 99.6 | 98.0 | 95.5 | 25 | 0.4 |
| Comparative Example 5 | 118.0 | 96.5 | 87.2 | 96.4 | 51 | 0.4 |
| Comparative Example 6 | 128.4 | 99.7 | 98.0 | 93.5 | 15 | 0.1 |
| Comparative Example 7 | 128.2 | 99.6 | 97.8 | 93.2 | 20 | 0.1 |
| Comparative Example 8 | 127.2 | 99.1 | 96.6 | 95.6 | 236 | 18.7 |
| Comparative Example 9 | 128.9 | 99.8 | 98.6 | 92.0 | 37 | 0.4 |
| Comparative Example 10 | 128.6 | 99.8 | 98.3 | 95.5 | 121 | 12.3 |

We claim:

1. A process for producing tetrabromobisphenol A of high quality, which comprises brominating bisphenol A with bromine, wherein a solvent mixture comprising a hydrohalogenic acid and an alcohol, is used as the solvent for reaction.

2. A process for producing tetrabromobisphenol A of high quality, which comprises brominating bisphenol A with bromine in an alcohol, wherein the reaction temperature is set at a level of from $-10°$ to $+20°$ C., and water is added in an aging step.

3. The process according to claim 2, wherein the amount of water added, is from 2 to 15% by weight relative to the solvent for reaction.

4. The process according to any one of claims 1 to 3, wherein the amount of bromine used, is from 4.0 to 5.0 mols per mol of bisphenol A.

5. The process according to claim 1, wherein the hydrohalogenic acid is hydrofluoric acid, hydrochloric acid, hydrobromic acid, hydroiodic acid or a mixture thereof, having a concentration of at least 5% by weight.

6. The process according to claim 1 or 2, wherein the alcohol is a $C_{1-4}$ alcohol.

7. The process according to claim 1, wherein the solvent mixture has a water concentration of from 3 to 20% by weight.

* * * * *